United States Patent
Jia et al.

(10) Patent No.: US 9,492,360 B2
(45) Date of Patent: *Nov. 15, 2016

(54) ENDODONTIC POST AND OBTURATOR

(75) Inventors: Weitao Jia, Wallingford, CT (US); Bruce Alpert, Madison, CT (US)

(73) Assignee: PENTRON CLINICAL TECHNOLOGIES, LLC, Wallingford, CT (US)

( * ) Notice: Subject to any disclaimer, the term of this patent is extended or adjusted under 35 U.S.C. 154(b) by 1454 days.

This patent is subject to a terminal disclaimer.

(21) Appl. No.: 11/623,390

(22) Filed: Jan. 16, 2007

(65) Prior Publication Data

US 2007/0148616 A1 Jun. 28, 2007

Related U.S. Application Data

(62) Division of application No. 10/279,609, filed on Oct. 24, 2002, now Pat. No. 7,204,874.

(60) Provisional application No. 60/336,500, filed on Oct. 24, 2001.

(51) Int. Cl.
*A61C 5/02* (2006.01)
*A61K 6/00* (2006.01)
*A61K 6/083* (2006.01)
*A61C 5/06* (2006.01)

(52) U.S. Cl.
CPC ........... *A61K 6/0023* (2013.01); *A61K 6/0038* (2013.01); *A61K 6/0085* (2013.01); *A61K 6/0091* (2013.01); *A61K 6/083* (2013.01); *A61C 5/02* (2013.01); *A61C 5/062* (2013.01)

(58) Field of Classification Search
USPC .................... 433/81, 102, 224, 220
See application file for complete search history.

(56) References Cited

U.S. PATENT DOCUMENTS

| 277,943 A | 5/1883 | Richmond |
| 644,297 A | 2/1900 | Metcalf |
| 674,419 A | 5/1901 | Kinsman |
| 1,312,120 A | 8/1919 | Hurtt |
| 1,463,963 A | 8/1923 | Miller |
| 1,469,992 A | 10/1923 | Card |
| 1,641,844 A | 9/1927 | Fisher |
| 1,649,508 A | 11/1927 | Carmichael |
| 3,066,112 A | 11/1962 | Bowen |
| 3,179,623 A | 4/1965 | Bowen |

(Continued)

FOREIGN PATENT DOCUMENTS

| DE | 3408503 | 9/1984 |
| DE | 3504472 | 7/1986 |

(Continued)

OTHER PUBLICATIONS

Notification of Transmittal of the International Preliminary Examining Report with date of mailing Oct. 4, 2001.

(Continued)

*Primary Examiner* — Ralph Lewis
(74) *Attorney, Agent, or Firm* — Cantor Colburn LLP (57) ABSTRACT

An obturator in which a filling material includes a biodegradable thermoplastic polymer. A bioactive substance may also be included in the filling material. The thermoplastic polymer acts as a matrix for the bioactive substance. The composition may include other polymeric resins, fillers, plasticizers and other additives typically used in dental materials.

7 Claims, 2 Drawing Sheets

(56) References Cited

U.S. PATENT DOCUMENTS

| | | |
|---|---|---|
| 3,194,784 A | 7/1965 | Bowen |
| 3,318,000 A | 5/1967 | Paris |
| 3,504,438 A | 4/1970 | Wittman et al. |
| 3,740,851 A | 6/1973 | Weissman |
| 3,751,399 A | 8/1973 | Lee et al. |
| 3,813,779 A | 6/1974 | Tosti |
| 3,855,702 A | 12/1974 | Malmin |
| 3,899,830 A | 8/1975 | Malmin |
| 3,919,774 A | 11/1975 | Fishman |
| 3,925,895 A | 12/1975 | Kliment et al. |
| 3,926,906 A | 12/1975 | Lee, II et al. |
| 3,949,479 A | 4/1976 | Malmin |
| 3,961,422 A | 6/1976 | Riitano et al. |
| 3,968,567 A | 7/1976 | Nevins |
| 3,981,736 A | 9/1976 | Broemer et al. |
| 4,050,156 A | 9/1977 | Chasanoff et al. |
| 4,131,597 A | 12/1978 | Bluethgen et al. |
| 4,171,544 A | 10/1979 | Hench et al. |
| 4,239,113 A | 12/1980 | Gross et al. |
| 4,253,829 A | 3/1981 | Adelberger |
| 4,253,835 A | 3/1981 | Ware |
| 4,343,608 A | 8/1982 | Hodosh |
| 4,407,675 A | 10/1983 | Hodosh |
| 4,425,094 A | 1/1984 | Tateosian et al. |
| 4,480,996 A | 11/1984 | Crovatto |
| 4,480,998 A | 11/1984 | Carse |
| 4,505,675 A | 3/1985 | Albert |
| 4,505,676 A | 3/1985 | Gonser |
| 4,518,356 A | 5/1985 | Green |
| 4,525,147 A | 6/1985 | Pitz |
| 4,538,989 A | 9/1985 | Apairo |
| 4,543,065 A | 9/1985 | Bushway |
| 4,544,359 A | 10/1985 | Waknine |
| 4,547,531 A | 10/1985 | Waknine |
| 4,595,713 A | 6/1986 | John |
| 4,605,415 A | 8/1986 | Richez |
| 4,622,012 A | 11/1986 | Smoler |
| 4,632,977 A | 12/1986 | Riazi |
| 4,645,503 A | 2/1987 | Lin et al. |
| 4,657,592 A | 4/1987 | Takubo |
| 4,681,545 A | 7/1987 | Lapcevic |
| 4,682,949 A | 7/1987 | Warrin |
| 4,684,555 A | 8/1987 | Neumeyer |
| 4,698,318 A | 10/1987 | Vogel |
| 4,704,088 A | 11/1987 | Newman |
| 4,717,341 A | 1/1988 | Goldberg et al. |
| 4,721,735 A | 1/1988 | Bennett |
| 4,738,616 A | 4/1988 | Reynaud |
| 4,740,245 A | 4/1988 | Futami et al. |
| 4,746,292 A | 5/1988 | Johnson |
| 4,758,156 A | 7/1988 | Johnson |
| 4,766,200 A | 8/1988 | Riazi |
| 4,775,646 A | 10/1988 | Hench |
| 4,783,429 A | 11/1988 | Shibuya |
| 4,801,528 A | 1/1989 | Bennett |
| 4,813,876 A | 3/1989 | Wang |
| 4,820,152 A | 4/1989 | Warrin et al. |
| 4,851,046 A | 7/1989 | Low et al. |
| 4,871,312 A | 10/1989 | Heath |
| 4,882,407 A | 11/1989 | Riazi |
| 4,894,011 A | 1/1990 | Johnson |
| 4,894,012 A | 1/1990 | Goldberg et al. |
| 4,902,649 A | 2/1990 | Kimura et al. |
| 4,931,096 A | 6/1990 | Fujisawa et al. |
| 4,934,934 A | 6/1990 | Arpaio, Jr. et al. |
| 4,936,775 A | 6/1990 | Bennett |
| 4,936,776 A | 6/1990 | Kwiatkowski |
| 4,950,697 A | 8/1990 | Chang |
| 4,952,150 A | 8/1990 | Schiwiora et al. |
| 4,966,952 A | 10/1990 | Riaza |
| 4,986,754 A | 1/1991 | Chang et al. |
| 5,051,093 A | 9/1991 | Fitzmorris |
| 5,064,373 A | 11/1991 | Staubli et al. |
| 5,067,900 A | 11/1991 | McSpadden |
| 5,073,112 A | 12/1991 | Weil |
| 5,074,792 A | 12/1991 | Bernadat |
| 5,074,916 A | 12/1991 | Hench |
| 5,083,923 A | 1/1992 | McSpadden |
| 5,085,586 A | 2/1992 | Johnson |
| 5,088,927 A | 2/1992 | Lee |
| 5,089,183 A | 2/1992 | Johnson |
| 5,092,773 A | 3/1992 | Levy |
| 5,098,298 A | 3/1992 | Johnson |
| 5,104,321 A | 4/1992 | Filhol |
| 5,104,322 A | 4/1992 | You |
| 5,106,298 A | 4/1992 | Heath |
| 5,118,297 A | 6/1992 | Johnson |
| 5,120,340 A | 6/1992 | Ducheyne et al. |
| 5,149,268 A | 9/1992 | Johnson |
| 5,154,611 A | 10/1992 | Calvin |
| 5,161,973 A | 11/1992 | Johnson |
| 5,165,893 A | 11/1992 | Thompson |
| 5,171,146 A | 12/1992 | Guerci |
| 5,181,850 A | 1/1993 | Neumeyer |
| 5,190,702 A | 3/1993 | Johnson |
| 5,204,106 A | 4/1993 | Schepers et al. |
| 5,215,461 A | 6/1993 | Riazi |
| 5,232,440 A | 8/1993 | Wilk |
| 5,232,878 A | 8/1993 | Kasuga et al. |
| 5,236,458 A | 8/1993 | Ducheyne et al. |
| 5,252,523 A | 10/1993 | Beall et al. |
| RE34,439 E | 11/1993 | Heath |
| 5,263,861 A | 11/1993 | Cohen et al. |
| 5,263,996 A | 11/1993 | Filhol |
| 5,275,562 A | 1/1994 | McSpadden |
| 5,276,068 A | 1/1994 | Waknine |
| 5,286,193 A | 2/1994 | Roane |
| 5,286,423 A | 2/1994 | Johnson |
| 5,302,129 A | 4/1994 | Heath et al. |
| 5,326,263 A | 7/1994 | Weissman |
| 5,328,367 A | 7/1994 | Johnson |
| 5,328,372 A | 7/1994 | Reynaud et al. |
| 5,336,642 A | 8/1994 | Wolcott |
| 5,372,759 A | 12/1994 | Johnson |
| 5,380,200 A | 1/1995 | Heath et al. |
| 5,382,161 A | 1/1995 | Roane |
| 5,382,284 A | 1/1995 | Arnold |
| 5,395,240 A | 3/1995 | Paschke et al. |
| 5,403,188 A | 4/1995 | Oxman et al. |
| 5,409,378 A | 4/1995 | Pohl |
| 5,415,547 A | 5/1995 | Torabinejad et al. |
| 5,429,996 A | 7/1995 | Kaneko |
| RE35,070 E * | 10/1995 | Fitzmorris .................... 433/224 |
| 5,464,362 A | 11/1995 | Heath et al. |
| 5,498,158 A | 3/1996 | Wong |
| 5,518,399 A | 5/1996 | Sicurelli, Jr. et al. |
| RE35,264 E | 6/1996 | Bennett |
| 5,525,646 A | 6/1996 | Lundgren et al. |
| 5,527,205 A | 6/1996 | Heath et al. |
| 5,540,766 A | 7/1996 | Castellani |
| 5,550,172 A | 8/1996 | Regula et al. |
| 5,552,454 A | 9/1996 | Kretschmann et al. |
| 5,564,929 A | 10/1996 | Alpert |
| 5,588,835 A | 12/1996 | Kert |
| 5,595,486 A | 1/1997 | Manocha |
| 5,605,460 A | 2/1997 | Heath et al. |
| 5,624,259 A | 4/1997 | Heath et al. |
| 5,624,976 A | 4/1997 | Klee |
| 5,628,674 A | 5/1997 | Heath et al. |
| 5,641,327 A | 6/1997 | Leas |
| 5,641,502 A | 6/1997 | Skalla et al. |
| 5,645,934 A | 7/1997 | Marcolongo et al. |
| 5,648,301 A | 7/1997 | Ducheyne et al. |
| 5,648,403 A | 7/1997 | Martin |
| 5,653,590 A | 8/1997 | Heath et al. |
| 5,655,950 A | 8/1997 | Heath et al. |
| 5,658,332 A | 8/1997 | Ducheyne et al. |
| 5,681,873 A | 10/1997 | Norton et al. |
| 5,700,901 A | 12/1997 | Hurst et al. |
| 5,713,736 A | 2/1998 | Heath et al. |
| 5,735,942 A | 4/1998 | Litkowski et al. |
| 5,741,139 A | 4/1998 | Sicurelli, Jr. et al. |
| 5,752,825 A | 5/1998 | Buchanan |
| 5,753,781 A | 5/1998 | Oxman et al. |

(56) References Cited

U.S. PATENT DOCUMENTS

| | | | |
|---|---|---|---|
| 5,756,559 A | 5/1998 | Blackwell et al. | |
| 5,762,497 A | 6/1998 | Heath | |
| 5,762,541 A | 6/1998 | Heath et al. | |
| 5,769,638 A | 6/1998 | Torabinejad et al. | |
| 5,797,748 A | 8/1998 | Reynaud et al. | |
| 5,803,736 A * | 9/1998 | Merritt, Jr. | 433/213 |
| 5,807,106 A | 9/1998 | Heath | |
| 5,816,816 A | 10/1998 | Scharf | |
| 5,827,060 A | 10/1998 | Zdarsky | |
| 5,833,457 A | 11/1998 | Johnson | |
| 5,833,458 A | 11/1998 | Harrisson, III | |
| 5,833,464 A | 11/1998 | Foser | |
| 5,882,196 A | 3/1999 | Kert | |
| 5,891,233 A | 4/1999 | Salonen et al. | |
| 5,914,356 A | 6/1999 | Erbe | |
| 5,915,970 A | 6/1999 | Sicurelli, Jr. et al. | |
| 5,919,044 A | 7/1999 | Sicurelli, Jr. et al. | |
| 5,921,775 A | 7/1999 | Buchanan | |
| 5,925,179 A | 7/1999 | Mannschedel | |
| 5,941,760 A | 8/1999 | Heath et al. | |
| 5,948,129 A | 9/1999 | Nonami et al. | |
| 5,955,529 A | 9/1999 | Imai et al. | |
| 5,964,592 A * | 10/1999 | Hites et al. | 433/221 |
| 5,977,204 A | 11/1999 | Boyan et al. | |
| 5,981,412 A | 11/1999 | Hench et al. | |
| 5,989,032 A | 11/1999 | Reynaud et al. | |
| 6,010,335 A * | 1/2000 | Kert | 433/81 |
| 6,012,924 A | 1/2000 | Reynaud et al. | |
| 6,024,565 A | 2/2000 | Sicurelli et al. | |
| 6,024,569 A | 2/2000 | Ohne et al. | |
| 6,025,414 A | 2/2000 | Rich | |
| 6,028,125 A | 2/2000 | Combe et al. | |
| 6,030,220 A | 2/2000 | Karmaker et al. | |
| 6,039,569 A | 3/2000 | Prasad et al. | |
| 6,054,400 A | 4/2000 | Brink et al. | |
| 6,074,209 A | 6/2000 | Johnson | |
| 6,086,374 A | 7/2000 | Litkowski et al. | |
| 6,106,296 A | 8/2000 | Johnson | |
| 6,110,205 A | 8/2000 | Nies | |
| 6,120,294 A | 9/2000 | Engelbrecht et al. | |
| 6,121,344 A | 9/2000 | Angeletakis et al. | |
| 6,121,381 A | 9/2000 | Deguchi et al. | |
| 6,126,446 A | 10/2000 | Mannschedel | |
| 6,130,178 A | 10/2000 | Andrus et al. | |
| 6,155,825 A | 12/2000 | Fischer et al. | |
| 6,162,056 A | 12/2000 | Mannschedel | |
| 6,171,986 B1 | 1/2001 | Zhong | |
| 6,183,253 B1 | 2/2001 | Billet et al. | |
| 6,186,791 B1 * | 2/2001 | Karmaker et al. | 433/220 |
| 6,214,048 B1 | 4/2001 | Ito et al. | |
| 6,220,863 B1 | 4/2001 | Kamohara et al. | |
| 6,224,377 B1 | 5/2001 | Bachmann et al. | |
| 6,224,662 B1 | 5/2001 | Nemeth | |
| 6,228,386 B1 | 5/2001 | Yang | |
| 6,244,871 B1 | 6/2001 | Litkowski et al. | |
| 6,248,344 B1 | 6/2001 | Ylanen et al. | |
| 6,254,392 B1 | 7/2001 | Mannschedel et al. | |
| 6,261,099 B1 | 7/2001 | Senia et al. | |
| 6,261,583 B1 | 7/2001 | Dunn et al. | |
| 6,264,471 B1 | 7/2001 | Martin | |
| 6,267,597 B1 | 7/2001 | Kim | |
| 6,287,122 B1 | 9/2001 | Seeram et al. | |
| 6,290,982 B1 | 9/2001 | Seppala et al. | |
| 6,293,795 B1 | 9/2001 | Johnson | |
| 6,299,905 B1 | 10/2001 | Peterson et al. | |
| 6,312,261 B1 | 11/2001 | Mays | |
| 6,331,112 B1 | 12/2001 | Lee | |
| 6,338,751 B1 | 1/2002 | Litkowski et al. | |
| 6,342,207 B1 | 1/2002 | Stoor et al. | |
| 6,353,041 B1 | 3/2002 | Qian | |
| 6,365,132 B1 | 4/2002 | Litkowski et al. | |
| 6,371,763 B1 | 4/2002 | Sicurelli, Jr. et al. | |
| 6,395,293 B2 | 5/2002 | Polson et al. | |
| 6,400,901 B2 | 6/2002 | Akami et al. | |
| 6,428,319 B1 | 8/2002 | Lopez et al. | |
| 6,431,863 B1 | 8/2002 | Sachdeva et al. | |
| 6,441,073 B1 | 8/2002 | Tanaka et al. | |
| 6,447,297 B1 * | 9/2002 | Lopez et al. | 433/224 |
| 6,455,608 B1 | 9/2002 | Jia et al. | |
| 6,461,420 B2 | 10/2002 | Ikuta | |
| 6,468,079 B1 | 10/2002 | Fischer et al. | |
| 6,472,454 B1 | 10/2002 | Qian | |
| 6,479,565 B1 | 11/2002 | Stanley | |
| 6,482,427 B2 | 11/2002 | Yang | |
| 6,482,444 B1 | 11/2002 | Bellantone et al. | |
| 6,511,748 B1 | 1/2003 | Barrows | |
| 6,520,774 B1 | 2/2003 | Mays | |
| 6,537,563 B2 | 3/2003 | Jia et al. | |
| 6,541,040 B2 | 4/2003 | Mhlbauer | |
| 6,566,418 B2 | 5/2003 | Imai et al. | |
| 6,568,937 B2 | 5/2003 | Kamohara et al. | |
| 6,602,516 B1 | 8/2003 | Martin | |
| 6,644,972 B1 | 11/2003 | Mays | |
| 6,787,584 B2 | 9/2004 | Jia et al. | |
| 6,852,656 B2 | 2/2005 | La Greca et al. | |
| 6,924,325 B2 | 8/2005 | Qian | |
| 6,946,143 B2 | 9/2005 | Kim et al. | |
| 6,986,662 B2 | 1/2006 | Haschke | |
| 6,997,714 B1 | 2/2006 | Schoeffel | |
| 7,021,936 B2 | 4/2006 | Koch et al. | |
| 7,086,864 B2 | 8/2006 | Lopez et al. | |
| 7,090,499 B1 | 8/2006 | Mays | |
| 7,090,720 B2 | 8/2006 | Kessler et al. | |
| 7,097,454 B1 | 8/2006 | Oh | |
| 7,097,455 B2 | 8/2006 | Koch et al. | |
| 7,204,874 B2 | 4/2007 | Jia et al. | |
| 7,204,875 B2 | 4/2007 | Jia et al. | |
| 7,211,136 B2 | 5/2007 | Jia et al. | |
| 7,303,817 B2 | 12/2007 | Jia | |
| 2002/0019456 A1 | 2/2002 | Jia | |
| 2002/0037258 A1 | 3/2002 | Dodd et al. | |
| 2002/0051952 A1 | 5/2002 | Kamohara et al. | |
| 2002/0072035 A1 | 6/2002 | Hickok | |
| 2002/0110787 A1 | 8/2002 | Abiru et al. | |
| 2002/0142261 A1 | 10/2002 | Van Den Houdt | |
| 2002/0147249 A1 | 10/2002 | Klee et al. | |
| 2002/0168615 A1 | 11/2002 | Kimmel | |
| 2002/0198283 A1 | 12/2002 | Imai et al. | |
| 2003/0045604 A1 | 3/2003 | Klee | |
| 2003/0105530 A1 | 6/2003 | Pirhonen et al. | |
| 2003/0114553 A1 | 6/2003 | Karim et al. | |
| 2003/0124482 A1 | 7/2003 | Calvert | |
| 2003/0207960 A1 | 11/2003 | Jia | |
| 2004/0006153 A1 | 1/2004 | Seppala et al. | |
| 2004/0018238 A1 | 1/2004 | Shukla | |
| 2004/0043053 A1 | 3/2004 | Yu et al. | |
| 2004/0048435 A1 | 3/2004 | Kim | |
| 2004/0065228 A1 | 4/2004 | Kessler et al. | |
| 2004/0086513 A1 | 5/2004 | Fairbrother et al. | |
| 2004/0087429 A1 | 5/2004 | Ogawa et al. | |
| 2004/0115589 A1 | 6/2004 | Karmaker et al. | |
| 2004/0131559 A1 | 7/2004 | Hauck | |
| 2004/0137075 A1 | 7/2004 | Fechner et al. | |
| 2004/0137403 A1 | 7/2004 | Koch et al. | |
| 2004/0137404 A1 | 7/2004 | Koch et al. | |
| 2004/0202986 A1 | 10/2004 | Hasche | |
| 2004/0248067 A1 * | 12/2004 | Lopez et al. | 433/220 |
| 2004/0249015 A1 | 12/2004 | Jia et al. | |
| 2004/0265783 A1 | 12/2004 | Karmaker et al. | |
| 2005/0003328 A1 | 1/2005 | Karmaker et al. | |
| 2005/0031703 A1 | 2/2005 | Beier et al. | |
| 2005/0042253 A1 | 2/2005 | Farrar et al. | |
| 2005/0079226 A1 | 4/2005 | Gonda et al. | |
| 2005/0079470 A1 | 4/2005 | Rutherford et al. | |
| 2005/0095303 A1 | 5/2005 | Krenitski et al. | |
| 2005/0112171 A1 | 5/2005 | Tang et al. | |
| 2005/0112528 A1 | 5/2005 | Wagner et al. | |
| 2005/0267232 A1 | 12/2005 | Klee | |
| 2005/0282108 A1 | 12/2005 | Goodis | |
| 2005/0282116 A1 | 12/2005 | Kusano | |
| 2006/0008766 A1 | 1/2006 | Fischer | |
| 2006/0024645 A1 | 2/2006 | Nordin | |
| 2006/0068362 A1 | 3/2006 | Desrosiers et al. | |
| 2006/0110703 A1 | 5/2006 | Bills | |

(56) References Cited

U.S. PATENT DOCUMENTS

| | | |
|---|---|---|
| 2006/0110704 A1 | 5/2006 | Bills |
| 2006/0154212 A1 | 7/2006 | Koch et al. |
| 2006/0154213 A1 | 7/2006 | Koch et al. |
| 2006/0171980 A1 | 8/2006 | Helmus et al. |
| 2007/0131139 A1 | 6/2007 | Jia et al. |
| 2007/0148616 A1 | 6/2007 | Jia et al. |
| 2007/0184405 A1 | 8/2007 | Jia et al. |
| 2008/0020353 A1 | 1/2008 | Jia |

FOREIGN PATENT DOCUMENTS

| | | |
|---|---|---|
| DE | 3512938 | 10/1986 |
| DE | 3513864 | 10/1986 |
| DE | 3839466 | 6/1989 |
| DE | 4103355 | 6/1992 |
| EP | 0539751 | 5/1993 |
| EP | 0329098 | 5/1994 |
| FR | 557756 | 8/1923 |
| FR | 1180326 | 12/1958 |
| FR | 2616653 | 6/1987 |
| FR | 2669211 | 5/1992 |
| FR | 2730627 | 8/1996 |
| GB | 1412077 | 10/1975 |
| WO | WO9314714 | 10/1993 |
| WO | WO9319687 | 10/1993 |
| WO | WO98/01493 | 1/1998 |
| WO | WO9811842 | 3/1998 |
| WO | WO9902201 | 1/1999 |
| WO | WO0067659 | 11/2000 |
| WO | WO02078646 | 10/2002 |
| WO | WO2004037214 | 5/2004 |
| WO | WO2004071326 | 8/2004 |
| WO | WO2004103319 | 12/2004 |
| WO | WO2005023132 | 3/2005 |
| WO | WO2005063171 | 7/2005 |
| WO | WO2006022747 | 3/2006 |
| WO | WO2006053936 | 5/2006 |
| WO | WO2006082078 | 8/2006 |

OTHER PUBLICATIONS

Notification of Transmittal of the International Preliminary Examination Report with date of mailing Jan. 24, 2005.
PCT Notification of Transmittal of the ISR and the Written Opinion of the International Searching Authority, Date of mailing: Apr. 1, 2005, ISR/WO PCT/US2004/028653.
Dentsply Product Information "Densfil" [http://www.mallefer.com/html/obturation.html] May 2001.
PCT Notification of Transmittal of the ISR or the Declaration with date of mailing Aug. 17, 2000.
Soft Core Dental Products Information "Soft Core" [http://www.variodent.at/grossha/022000/soft-core.html] May 2001.
Dentsply Production Information "Thermasystem Plus Obturation System" [http://www.xray.essix.com/endodontics/endomain.html] May 2001.
Product Information for Tone P757 Polymer, Form No. 321-00050, Dow Chemical Company, Dec. 2001.
Product Information for Tone P767 Polymer, Form No. 321-00051, Dow Chemical Company, Dec. 2001.
Product Information for Tone P787 Polymer, Form No. 321-00052, Dow Chemical Company, Dec. 2001.
Shipper et al., An Eval. of Microbial Leadage in Roots Filled with a Thermoplastic Synth. Polymer-Based Root Canal Filling Mat., J. of Endod. vol. 30, No. 5, May 2004, 342-347.
Teixeira et al., "Fracture Resistance of Roots Endodontically Treated with a New Resin Filling Material", JADA 2004; 135: 646-652.
Nahmias Y., Serota K.S., Watson, Jr. W.R., "Predictable Endodontic Success: Part II—Microstructural Replication", Oral Health Journal, Dec. 2003.
Mounce R., Glassman G., "Bonded Endodontic Obturation: Another Quantum Leap Forward for Endodontics", Oral Health Journal, Jul. 2004.
Chivian N., "Resilon—The Missing Link in Sealing the Root Canal", Compendium, vol. 25, No. 10A, Oct. 2004, pp. 823-825.
Barnett F., Trope M., "Adhesive Endodontics: Combining Technologies for Enhanced Success", Dentaltown, vol. 5, Issue 8, Aug. 2004, pp. 34, 36, 38.
Goff, S. "Easier Endo, a DPR survey report", Dental Products Report, Sep. 2004, pp. 14, 15, 16, 17, 18, 20.
Raina et al., "Comparison of Microleakage of Two Obturation Materials", Abstract #18, 31(3) Mar. 2005, Journal of Endodontics.
Shipper et al, "Periapical Inflammation after Coronal Microbial Inoculation of Dog Roots Filled with Gutta-Percha or Resilon", J. of Endodontics, vol. 31, No. 2, Feb. 2005, 91-96.
Stratton et al., A Fluid Filtration Comparison of Gutta-Percha Versus Resilon: A New Soft Resin Endodontic Obturation System, Abst. #20, 31(3), Mar. 2005, Journal of Endodontics.
Tay et al, "Bonding of Self-Etching Primer/Polycaprolactone-Based Root-Filling Material to Intraradicular Dentin", Abst.: 2005 IADR/AADR/CADR 83rd General Session & Exhibition.
Jia W, Gagliardi S, Jin S, "Bondability of Resilon to a Root Canal Sealant", Abstract: 2005 IADR/AADR/CADR 83rd General Session & Exhibition.
Li Y. et al., "Antimicrobial Potential of Epiphany RCS System", Abstract: 2005 IADR/AADR/CADR 83rd General Session & Exhibition.
Benzley LP et al., "Characterization of Tubule Penetration Using Resilon: A Soft-Resin Obturation System", Abstract: 2005 IADR/AADR/CADR 83rd General Sessio.
Barnett F et al., "Resilon: A Novel Material to Replace Gutta Percha", Contemporary Esthetics and Restorative Practice, Aug. 2005, vol. 9, No. 8, pp. 64-67.
Gambarini G et al., "Apical Leakage of a New Obturation Technique", Abstract #12, 31(3), Mar. 2005, Study by Gambarini and Pongione in the Journal of Endodontics.
U.S. Appl. No. 10/279,609, filed Oct. 24, 2002; Non-Final Rejection dated Dec. 14, 2004.
U.S. Appl. No. 10/279,609, filed Oct. 24, 2002; Non-Final Rejection dated Jul. 5, 2005.
U.S. Appl. No. 10/279,609, filed Oct. 24, 2002; Amendment dated Nov. 3, 2005.
U.S. Appl. No. 10/279,609, filed Oct. 24, 2002; Final Rejection dated Dec. 20, 2005.
U.S. Appl. No. 10/279,609, filed Oct. 24, 2002; Non-Final Rejection dated Jun. 21, 2006.
U.S. Appl. No. 10/279,609, filed Oct. 24, 2002; Amendment dated Oct. 10, 2006.
U.S. Appl. No. 10/304,371, filed Nov. 26, 2002; Non-Final Rejection dated Feb. 17, 2005.
U.S. Appl. No. 10/304,371, filed Nov. 26, 2002; Amendment dated May 11, 2005.
U.S. Appl. No. 10/304,371, filed Nov. 26, 2002; Non-Final Rejection dated Jul. 5, 2005.
U.S. Appl. No. 10/304,371, filed Nov. 26, 2002; Amendment dated Nov. 3, 2005.
U.S. Appl. No. 10/304,371, filed Nov. 26, 2002; Final Rejection dated Dec. 20, 2005.
U.S. Appl. No. 10/304,371, filed Nov. 26, 2002; Amendment dated Jan. 19, 2006.
U.S. Appl. No. 10/304,371, filed Nov. 26, 2002; Non-Final Rejection dated Jun. 21, 2006.
U.S. Appl. No. 10/304,371, filed Nov. 26, 2002; Amendment dated Oct. 10, 2006.
U.S. Appl. No. 10/465,416, filed Jun. 18, 2003; Non-Final Rejection dated Sep. 22, 2005.
U.S. Appl. No. 10/465,416, filed Jun. 18, 2003; Amendment filed Feb. 21, 2006.
U.S. Appl. No. 10/465,416, filed Jun. 18, 2003; Non-Final Rejection dated Apr. 18, 2006.
U.S. Appl. No. 10/465,416, filed Jun. 18, 2003; Amendment dated May 8, 2006.

(56) References Cited

OTHER PUBLICATIONS

U.S. Appl. No. 10/465,416, filed Jun. 18, 2003; Non-Final Rejection dated Jun. 21, 2006.
U.S. Appl. No. 10/465,416, filed Jun. 18, 2003; Amendment dated Oct. 10, 2006.
U.S. Appl. No. 10/914,057, filed Aug. 06, 2004; Non-Final Rejection dated Jul. 3, 2007.
U.S. Appl. No. 10/914,057, filed Aug. 06, 2004; Amendment dated Jul. 24, 2007.
U.S. Appl. No. 11/614,233, filed Dec. 21, 2006; Non-Final Rejection dated Feb. 3, 2009.
U.S. Appl. No. 11/614,233, filed Dec. 21, 2006; Amendment dated May 1, 2009.
U.S. Appl. No. 11/671,079, filed Feb. 5, 2007; Non-Final Rejection dated Jul. 8, 2009.
U.S. Appl. No. 11/671,079, filed Feb. 5, 2007; Amendment filed Nov. 9, 2009.
U.S. Appl. No. 11/857,528, filed Sep. 17, 2007; Non-Final Rejection dated Aug. 10, 2009.
U.S. Appl. No. 11/857,528, filed Sep. 17, 2007; Amendment dated Nov. 9, 2009.
Final Office Action dated Mar. 16, 2010 for U.S. Appl. No. 11/857,528.
Final Office Action dated Mar. 17, 2010 for U.S. Appl. No. 11/671,079.
Response to Final Office Action dated May 5, 2010 for U.S. Appl. No. 11/671,079.
Response to Final Office Action dated May 5, 2010 for U.S. Appl. No. 11/857,528.

\* cited by examiner

ENDODONTIC POST AND OBTURATOR

CROSS-REFERENCE TO RELATED APPLICATIONS

This application is a divisional of U.S. application Ser. No. 10/279,609 filed Oct. 24, 2002 which claims priority to provisional Application Ser. No. 60/336,500 filed Oct. 24, 2001 all of which are hereby incorporated by reference.

FIELD OF THE INVENTION

This invention relates to filling materials for use in root canal treatments.

BACKGROUND OF THE INVENTION

Endodontics or root canal therapy is that branch of dentistry that deals with the diseases of the dental pulp and associated tissues. One aspect of endodontics comprises the treatment of infected root canals, the removal of diseased pulp tissues, followed by the biomechanical modification and the subsequent filling of the pulp canal (root canal). Root canal therapy is generally indicated for teeth having sound external structures but having diseased, dead or dying pulp tissues. Such teeth may or may not generally possess intact enamel and dentin and are satisfactorily engaged with bony tissue. In such teeth, the pulp tissue and excised portions of the root should be replaced by a biocompatible substitute. One technique for the preparation of a root canal involves creating a coronal access opening with a conventional dental drill. A tool is used for gross removal of pulp material from the root canal through the coronal access opening. The void formed is enlarged with reamers and/or files to result in a fully excavated cavity. Debris is removed from this cavity by flushing and the cavity is cleansed to remove all diseased tissue. Following chemical antisepsis, the excavated canal is ready for filling.

A basic method involves inserting a filling cone into a root canal and cementing therein to obturate the canal. The common root canal filling cone material is made from gutta percha. Lateral condensation is a method in which several filling cones, a primary cone and auxiliary cones, are inserted into a root canal. The primary cone is inserted and cemented to the seat of the root canal. Using a tapered spreader, the primary cone is then squeezed against the side of the root canal and a second cone is inserted and cemented into place. This process is continued until the root canal is completely obturated which can require up to 10 to 15 filling cones. Vertical condensation of warm or hot gutta percha is yet another method of sealing root canals. After cementing a primary cone short of the apex of the root canal, heat application is alternated with a series of smaller and smaller pluggers until the gutta percha is moved to the apex. This is often possible when the smallest plugger approaches the apex of the tooth within 3 to 5 millimeters. The space is then backfilled. Lateral canals are packed and sealed as a consequence of lateral expansion of a wave of heated gutta percha. Alternatively, small segments of gutta percha can be used in this method that are inserted into the root canal, heated in order that they can adhere to one another and each backfilled one at a time until the root canal is filled. All three of these methods, the single filling cone, lateral condensation and vertical condensation apply root canal cement or sealer around the individual cones or in between segments as a binding agent.

Another method employs an injection gun that injects warm or hot gutta percha filling material into a root canal. The injector initially places heated gutta percha at the apical area of the root canal through a needle-like canula tip and fills the gutta percha into any surrounding voids/spaces under pressure or at the seat of the root canal which is then condensed with a plugger into the root tip. The injector then backfills the root canal by injecting additional gutta percha into the root canal until it is obturated. A similar method involves heating gutta percha on a flexible metal or plastic carrier used to insert the gutta percha into the root canal. The carrier may be a solid rod, or a hollow rod, situated in the center of a master cone. The rod is connected to a handle which may be removed by slipping it out of the hollow rod, or cutting it off if it is a solid rod.

Most of the current methods employed in obturating a canal use a gutta percha material that is inert in nature and will not be absorbed or degraded by the living tissue if the root canal is overfilled and extends beyond the apex. It has been a challenge for dentists to control the exact amount of the material within the border of the root canal to avoid overfilling. Moreover, gutta percha material is a polyisoprene rubber material in nature, which does not have the capability to bond to most of the dental materials, especially when the root canal sealer is a polymer-based material. Gutta percha exhibits poor strength and brittleness. Dental gutta percha points/cones tend to break in harsh conditions, e.g., sharply curved root canals, tight spaces during a root canal treatment, and the like.

It is desirable to provide a root canal filling material that bonds easily to sealants. It is preferable that the root canal filling material have proper strength and flexibility. It would be beneficial that the root canal filling material be bioactive.

SUMMARY OF THE INVENTION

These and other objects and advantages are accomplished by the filling material of the present invention comprising a biodegradable thermoplastic polymer. A bioactive substance may be combined with the biodegradable thermoplastic polymer. The thermoplastic polymer acts as a matrix for the bioactive substance. The composition may include other polymeric resins, fillers, plasticizers and other additives typically used in dental filler materials.

The filling material is used for the filling of root canals. The material may be placed in a root canal that has been opened to a predetermined dimension by use of endodontic files, to seal the apical end. If necessary, the filling material can be compacted toward the apex, while it is still in the softened state, to ensure the apex is adequately sealed. If, by chance, the filling material is pushed slightly past the apex, or seeps through the apex, or comes in contact with fluids in the mouth, the biodegradable material will disintegrate or break down and be absorbed or partially absorbed by the surrounding living tissues. If a bioactive substance is present in the filling material, it will react with the tissue in the mouth, mending and/or growing tissue to fill in any gaps or openings.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

As will be appreciated, the present invention provides a filling material for a root canal comprising a biodegradable thermoplastic polymer. A bioactive substance may be combined with the biodegradable thermoplastic polymer. The thermoplastic polymer acts as a matrix for the bioactive substance. The composition may include other polymeric resins, fillers, plasticizers and other additives typically used in dental filler materials including, but not limited to, antibiotic, cariostatic, antibacterial, or other anti-inflammatory, biologically active, therapeutic materials, pigments and dyes.

Suitable thermoplastic polymers for use as the matrix are pharmaceutically compatible and biodegradable by cellular action and/or by the action of body fluids. Examples of appropriate thermoplastic polymers include but are not limited to polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, polyethylene oxides, polyacrylates/methacrylates, poly(malic acid) polymers, polymaleic anhydrides, poly(methylvinyl) ethers, poly(amino acids), chitin, chitosan, and copolymers, terpolymers, or combinations or mixtures of the above materials.

Preferred materials are the polylactides, polyglycolides, polycaprolactones, and copolymers thereof. These polymers can be used to advantage in the polymer system in part because they show excellent biocompatibility. They produce little, if any, tissue irritation, inflammation, necrosis, or toxicity. In the presence of water, these polymers produce lactic, glycolic, and hydroxycaproic acid, respectively, which are readily metabolized by the body. The polylactides and polycaprolactones can also incorporate glycolide monomer to enhance the resulting polymer's degradation. The biodegradable thermoplastic polymer may be present in an amount from about 10 to about 100 percent by weight.

The bioactive material may include any substance or metabolic precursor thereof, which is capable of promoting growth and survival of cells, tissues, and bone. Suitable bone growth promoting substances include but are not limited to bioglass, calcium phosphate, Portland cement, hydroxyapatite, tricalcium phosphate, a di- or polyphosphonic acid, an anti-estrogen, a sodium fluoride preparation, a substance having a phosphate to calcium ratio similar to natural bone, calcium hydroxide, other suitable calcium-containing compounds, and the like. A bone growth promoting substance may be in the form of a particulate or fiber filler in nano, micro or macro form, or mixtures thereof, bone chips, bone crystals or mineral fractions of bone and/or teeth, a synthetic hydroxyapatite, or other suitable form. The bioactive filler may be present in an amount of up to about 90 percent by weight.

The biodegradable thermoplastic polymers should have melting temperatures of about 50 to about 300° C., preferably about 60 to about 250° C., and most preferably about 70 to about 200° C. The melting temperature of the polymers in these ranges facilitates the process of compounding the thermoplastic polymer with bioactive inorganic particulates and other additives. Furthermore, the melting temperature range of the polymers also facilitates the application of the filling material made from the compounds into a root canal with conventional accessible heating methods.

Examples of additional polymeric resins useful in the filling composition include, but are not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to "UDMA", triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") and the like. Among the examples given, the resins containing surface functional groups such as acrylate/methacrylate, epoxy, hydroxyl and others are preferred since they not only serve as plasticizers for the compositions but as adhesive components as well for promoting the bonding between the compound and a sealant. Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine (which are herein incorporated by reference). An especially preferred methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA").

Other fillers which may be used in addition to the bioactive material include inorganic and organic particulates and fibrous fillers known in the art including, but are not limited to, silica, silicate glass, quartz, zinc oxide, barium sulfate, barium silicate, strontium silicate, barium borosilicate, strontium borosilicate, borosilicate, lithium silicate, amorphous silica, bismuth compounds such as BiOCl, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference). Some of the fillers also act as radiopaque/high refractive index materials, such as apatites, silica glass fillers, calcium silicate based fillers, hydroxyapatites, barium sulfate and bismuth subcarbonate. Fibrous fillers also include, but are not limited to, include glass, ceramic, metal, carbon, graphite, polymeric such as cellulose, polyamide, aramid, polyester, polyaramid, acrylic, vinyl and modacrylic, polyolefin, polytetrafluorethylene, mixtures thereof, as well as other fibers known in the art. The fibers may be of uniform or random length, unidirectional or multidirectional, or randomly dispersed, and may be as short as about 3 to about 4 millimeters (mm) or shorter. The fibers may also be in the form of fabric as set forth in U.S. Pat. No. 6,186,791, or as possible reinforcing fibers, as used in U.S. Pat. Nos. 4,717,341 and 4,894,012 to Goldberg et al., all of which are hereby incorporated by reference.

Examples of plasticizers useful in the filling composition include, but are not limited to, polyol, polyolfin or a mixture thereof. The plasticizer can be incorporated into the composition in the range of up to about 40 percent by weight, preferably up to about 30 percent by weight, and most preferably up to about 20 percent by weight.

The following examples illustrate the invention.

Example 1

A composition comprising polycaprolactone available from Union Carbide in an amount of about 40%, a bioactive glass having a composition similar to Bioglass™ (made by U.S. Biomaterials) in an amount of about 30%, USP grade zinc oxide in an amount of about 20% and barium sulfate as a radio-opacifying agent in an amount of about 10% was manufactured. The method of forming the composition involved heating the polycaprolactone at about 70° C. to a softened state. The remaining ingredients were then added and mixed under the action of kneading, pressing, or mixing to blend into the polycaprolactone completely to form a homogenous dough. The formed compound was then ready for application to the carrier device.

Example 2

A composition comprising polycaprolactone in an amount of about 30%, caprolactone (methacryloxy)ethyl ester (CMEE) in an amount of about 10%, tricalcium phosphate in an amount of about 30%, and zirconium oxide in an amount of about 10% was manufactured. The method of forming the composition involved heating the polycaprolactone (available from Union Carbide) at about 70° C. to a softened state. The remaining ingredients were then added and mixed under the action of kneading, pressing, or mixing to blend into the polycaprolactone completely to form a homogenous dough. The formed compound was then ready for application to the carrier device.

The following Table 1 sets forth examples of the filling material compositions made similar to the methods described in Examples 1 and 2 above.

TABLE 1

| | Composition WEIGHT (%) | | | | |
|---|---|---|---|---|---|
| | A | B | C | D | E |
| P767* | 40 | 30 | 21 | 25 | |
| P787* | | | 9 | | 27 |
| PEGDMA(400) | | | 5 | | 8 |
| UDMA | | | | 10 | |
| CMEE** | | 10 | | | |
| Bioactive glass | 30 | 10 | 21.5 | | 30 |
| ZnO | 20 | 10 | 21.5 | 25 | 25 |
| BaSO$_4$ | | | 20 | 22 | 20 |
| BiOCl | | 10 | | | |
| Ca(OH)$_2$ | | | | 20 | |
| Ca$_3$(PO$_4$)$_2$ | | 20 | | | |
| ZrO$_2$ | | | | | 10 |

*P767 and P787 are polycaprolactone resins sold under the trade name of TONE™ POLYMER by Dow Chemical Co.
**CMEE is caprolactone (methacryloxy) ethyl ester The compositions were then prepared for bonding strength tests as follows:

Sample Preparation for Bonding Tests

The compositions from Table 1 above were softened at about 80° C. in a convection oven. While the materials were at a workable consistency, they were placed in 15 mm diameter and 1.2 mm thickness steel molds between two glass slides and were cooled down to bench temperature. Sample disks were formed and the glass slides and molds were removed. Some trimming was necessary to remove the flashes from the edge. Five discs were prepared for each test material.

The sample disks were then mounted into a cold-cured acrylic mounting material in a splitable cylindrical TEFLON™ mold of a 20 mm diameter and about a 30 mm height, leaving one side of the disk exposed. A two-component self curable A2 shaded Cement-It™ C&B Universal Cement (Pentron Corp., Wallingford, Conn.), which is a methacrylate resin cement, was used to make a composite button and was bonded directly to the exposed sample surfaces. Number five (#5) Gelatin capsules (Torpac Inc. N.J.) were used to load the cement and were placed directly onto the surfaces under a load of 500 grams on a Bencor testing device (Denville Engineering, Calfi.) until the cement hardened. The cement has a setting time of approximately 4 minutes after the two components are mixed. After one hour of bench setting, the bonded samples were debonded with a push shear mold in a Bencor test device under a crosshead speed of 0.02 in/minute. The maximum load at which the cement cylinders broke from the sample surfaces was recorded. Bonding strengths were calculated using the load divided by the contact surface area of the cement cylinder.

The following Table 2 sets forth bonding strengths of the filling compositions in Table 1 along with a gutta percha composition for comparison.

TABLE 2

| Compositions | Bond Strength, MPa (S.D.) |
|---|---|
| A | 3.2 (1.1) |
| B | 5.5 (2.3) |
| C | 6.5 (1.9) |
| D | 6.8 (0.7) |
| E | 6.8 (1.2) |
| Gutta Percha Control* | 0 (Samples all failed before testing) |

*The control is a dental gutta percha material available from Endodent, Inc. Duart, CA Transverse Deflection Tests To test the flexibility of the compositions herein, a testing apparatus for the transverse deflection test as described in ADA specification Number 12 for Denture Base Polymers was adopted for the test. The test samples were made into bars of 50×3×3 mm in a TEFLON splitable mold while the materials were at a soft stage. A 500 gram weight was applied onto the center of the test sample through the loading nose. The span between the two supports was 30 mm. The still load was removed after one minute (if the sample had not broken during the standing period) and the maximum deflection distance was measured and recorded. Three test samples were run for each test material. The test results are shown in Table 3.

TABLE 3

| Compositions | Maximum Deflection Distance (mm) | Time of Test Samples withstanding the load) |
|---|---|---|
| A | 6-8 | Full minute without break |
| C | 7-9 | Full minute without break |
| Gutta Percha Control | 1-3 | 1-2 seconds (Broke almost instantly after applied the load) |

The results of the inventive materials are shown to have superior results over the gutta percha material.

The bioactive material can be miscible in the polymer to provide a homogeneous mixture with the polymer, or insoluble in the polymer to form a suspension or dispersion with the polymer. The filling material may be in the form of a cone to be inserted into a canal. The cone may be inserted into the canal using a file or similar instrument, or it may be attached to a file, shaft or similar carrier which instrument is then inserted into the canal with the cone thereon. After insertion, the carrier is removed or the excess of the cone is cut off as in a conventional gutta percha cone application from the root canal.

Alternatively, the material may be softened and compacted toward the apex, while it is still in the softened state, to ensure the apex is adequately sealed. This may be done by a backfilling technique whereby, for example, the material is heated and injected into the canal using a device having a needle, such as the Obtura TI device available from Obtura/Spartan, Fenton, Mo.

If, by chance, the filling material is pushed slightly past the apex, or seeps through the apex, or comes in contact with fluids in the mouth, the biodegradable material will disintegrate or break down and be absorbed or partially absorbed by the surrounding living tissues and the bioactive substance present in the filling material will react with tissue in the mouth, mending and/or growing tissue to fill any gaps or openings.

Commonly assigned U.S. Pat. No. 6,455,608 is directed to dental compositions comprising degradable polymers for use as root canal sealants, implants and pulp capping materials and is hereby incorporated by reference. The compositions use polymerizable and degradable macromonomers to provide precursors for forming biodegradable and biocompatible polymers upon a chemical reaction, which advantageously allow for tissue regrowth.

As yet another alternative, the filling material may be integrally formed on a post whereby a single post unit comprises a combined endodontic post and tip of filling material. To use the post unit, the tip of the device is softened by placing in an oven or heater to heat and soften the filling material or chemically treating to soften the material. The device will then be placed in a root canal that has been opened to a predetermined dimension by use of endodontic files, to seal the apical end. If necessary, the filling material can be compacted toward the apex, while it is still in the softened state, to ensure the apex is adequately sealed. The post may then be cemented into place by lining the canal walls with a bonding agent and filling the interface between the post and the walls of the canal with a resin cement such as a dual cure cement, a light cure cement or a self cure cement such as FiberFill™ RCS root canal sealant or Cement-It® Universal cement, both available from Pentron Clinical Technologies, LLC in Wallingford, Conn. This will result in a coronal seal of the canal via a resin restorative material and an apical seal of the canal by means of a filling material and sealant. The remaining portion of the post, extending supra-gingivally, will be used to build a core around it. Any excess will be cut off. One length of the device will be longer to accommodate the longer roots in anterior teeth. Another length will be shorter to accommodate smaller roots in the molar region. Various diameters may also be provided to accommodate the different sizes of root canals. The bonded flexible post may strengthen the tooth to prevent subsequent root fractures.

Figure 1:
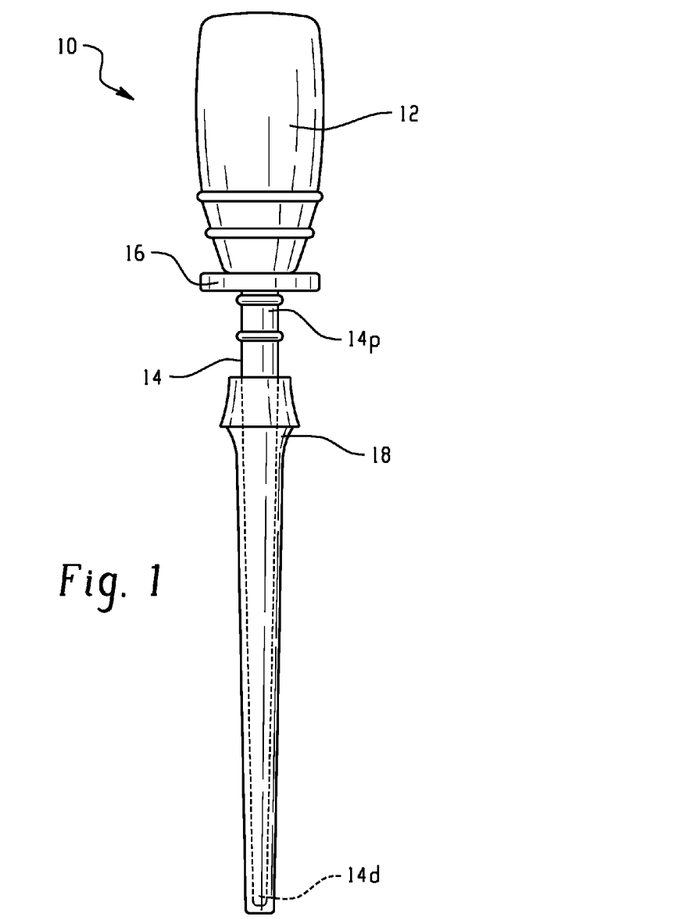
FIG. 1 is an elevational view of an appliance having a filling material thereon.

Reference is made to FIGS. 1 through 4 which show carriers having the filling material applied to the tip of the carrier. FIG. 1 shows an appliance 10 having a handle 12 and an elongated shaft 14. Shaft 14 has a proximal end 14p and a distal end 14d that fits in a root canal. A sliding support 16 is positioned between shaft 14 and handle 12 to serve as an indicator of the depth of the canal and to help maintain the carrier in place. After the appliance is inserted in the canal, sliding support 16 is moved to the point at the top of the canal. Filling material 18, containing a biodegradable thermoplastic polymer and a bioactive filler, is positioned on the shaft, starting at the proximal end and continuing down, over the distal end.

Figure 2:
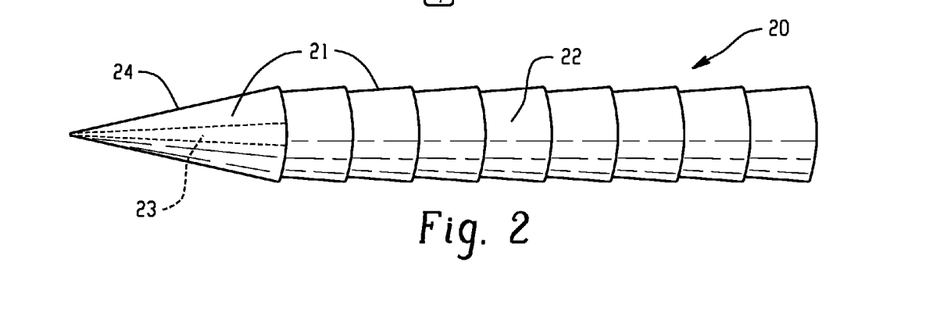
FIG. 2 is an elevational view of a post as an alternate carrier in accordance with the invention.

Turning to FIG. 2, a post unit 20 is shown comprising a post section 21 and a cone or tip section 24. Tip section 24 comprises a flexible rod or cone comprising a biodegradable thermoplastic polymer in combination with a bioactive substance for filling the apex of the canal. The filling material may include additives typical in the dental field such as plasticizing, antibiotic, cariostatic, antibacterial, or other anti-inflammatory, biologically active or therapeutic materials.

Post section 21 comprises a main body or endodontic portion 22 and a carrier or apical portion 23 which is located at the apical end of post unit 20. Main body 22 may be a solid rod of circular or other suitable cross-section comprising a substantially smooth surface or may comprise a plurality of frustoconical sections arranged coaxially along the longitudinal axis of main body 22. Preferably, main body 22 has consistent width along the longitudinal axis thereof whereas frustoconical sections each have the same tapered width and same length. It is possible to vary the width and/or length of main body 22 and/or vary the tapered width and/or length of frustoconical sections along the longitudinal axis of main body 22.

Carrier 23 is preferably an extension of main body 22 of post section 21 and is of very fine diameter to accommodate tip section 24 of thermoplastic material of post unit 20. In one method of manufacture which will be discussed hereinafter, post section 21 is manufactured from a rod of material that is cut or machined at the apical end to result in carrier 23 having a very small width or diameter in comparison to main body 22. Carrier 23 is of small diameter to allow enough area to form tip section 24 thereon, and also of enough strength and integrity to accommodate the filling material as discussed above. As stated above, carrier 23 is preferably an extension of main body 22 and is shown having constant diameter along the length thereof, but may be of any shape or size sufficient to hold tip section 24 thereon.

Post section 21 may be fabricated of any material to provide a flexible apical portion and a more rigid endodontic and/or coronal or supracoronal portion, such as metal, plastic, ceramic, polymeric, composite, or other material suitable for placement in the mouth. Composite materials include but are not limited to filler reinforced composite materials and fiber reinforced composite materials comprising the reinforcing component in a polymeric matrix material such as those composite materials listed in U.S. Pat. Nos. 4,717,341 and 4,894,012 to Goldberg et al., U.S. Pat. No. 6,039,569 to Prasad et al., U.S. Pat. No. 6,030,220 to Karmaker et al, U.S. Pat. No. 5,564,929 to Alpert, and U.S. Pat. No. 5,919,044 to Sicurelli, Jr. et al., all of which are hereby incorporated by reference. The fiber reinforced composite material may comprise fibers in the form of long, unidirectional, continuous filaments which are preferably at least partially aligned and oriented along the longitudinal dimension of the component with alignment normal or perpendicular to that dimension also possible. The fibers may be of uniform or random length, unidirectional or multidirectional, or randomly dispersed, and may be as short as about 3 to about 4 millimeters (mm) or shorter. The fibers may also be in the form of fabric as set forth in copending Ser. No. 09/280,760 filed Mar. 29, 1999, now U.S. Pat. No. 6,186,791, and may include any of the attributes of the post described therein, the contents all of which are hereby incorporated by reference. Due to the improved structural integrity, the amount of fibers in the structural component preferably equals at least about 20% by weight (wt %) and preferably about 20 wt % to about 70 wt %. Possible reinforcing fibers, which are preferably used in accordance with U.S. Pat. Nos. 4,717,341 and 4,894,012 to Goldberg et al. (which are herein incorporated by reference), include glass, ceramic, metal, carbon, graphite, polymeric such as cellulose, polyamide, aramid, polyester, polyaramid, acrylic, vinyl and modacrylic, polyolefin, polytetrafluorethylene, mixtures thereof, as well as other fibers known in the art. One preferred version of the device is comprised of unidirectional microfilamentous glass fibers bundled in a resin matrix.

In order to enhance the bond between the fibers and polymeric matrix, thereby enhancing the reinforcing effect, the fibers may be silanized or otherwise treated such as by grafting functional monomers to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl tri-methoxy silane), produced by OSI Specialties, New York. The polymeric matrix is selected from those known in the art of dental materials, including, but not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine (which are herein incorporated by reference). An especially preferred methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA"). The polymer matrix, which typically includes polymerization initiators, polymerization accelerators, ultra-violet light absorbers, anti-oxidants, fluorescent whitening agents, free radical initiators, and/or other additives well known in the art, may be visible light curable, self-curing, dual curing, or vacuum, heat, or pressure curable compositions, as well as any combination thereof. Heat and pressure or vacuum curable compositions include a heat cure initiator such as benzoyl peroxide, 1,1'-azobis(cyclohexanecarbo-nitrile) or other free radical initiators. The preferred polymeric matrix is a light and heat curable matrix, wherein light effects partial cure of the polymer matrix, while final curing is by heat under controlled atmosphere.

Fillers may be present in addition to or instead of fibers in an amount up to about 80 wt %, and preferably about 70 wt %. If fibers are present, the amount of filler is present in an amount of up to about 30 wt % of one or more fillers known in the art and used in dental restorative materials. Suitable fillers include those capable of being covalently bonded to the polymeric matrix itself or to a coupling agent that is covalently bonded to both. Fillers include silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include silanes, zirconates, and titanates. If the post is manufactured from a composite material, it is preferably in completely cured or hardened state.

Examples of metals useful as post section 21 include but are not limited to metals or alloys of Pd, Pt, Rh, Ir, Au, Ag, Ti, Co, Mo and mixtures thereof such as AgPd, AuPtPd, TiAlFe, TiAlV, CoCrMo, stainless steel and brass. Ceramic materials useful in the fabrication of post section 21 include but are not limited to alumina, zirconia, mullite, spinel, porcelain, titania, lithium disilicate, leucite, amorphous glass, lithium phosphate, and combinations thereof, or any high strength ceramic material which can withstand the stresses created in the mouth.

Carrier 23 preferably comprises a smooth surface, although it is in no way limited to such and may be of any surface suitable for application of filling material thereon. The post may be provided in an opaque tooth color or it may be colored similar to a tooth's pulp for enhanced esthetics. The post may include an appropriate amount of radiopaque material such as titanium oxide, barium sulfate, and similar materials known in the dental industry to insure x-ray documentation which may be added to the post material during manufacture thereof.

After post section 21 has been manufactured, carrier 23 of post section 21 is then coated with a filling material such as set forth above to obtain cone section 24 thereon. The filling material may be applied by any known means such as dipping, injection molding, hand rolling, and the like.

To use the post unit, the device may be used as is, or may be heated by placing in or near an oven or heater to heat and soften the filling material or dipped in a chemical solution such as chloroform to soften the filling material. The device will then be placed in a root canal that has been opened to a predetermined dimension by use of endodontic files, to seal the apical end. If necessary, the filling material can be compacted toward the apex, while it is still in the softened state, to ensure the apex is adequately sealed. The post is then cemented into place by lining the canal walls with a bonding agent and filling the interface between the post and the walls of the canal with a resin cement, such as a dual cure cement. This will result in a coronal seal of the canal via resin restorative material and an apical seal of the canal by means of filling material and sealant. The remaining portion of the post, extending supra-gingivally, will be used to build a core around it, and if necessary, for placement of a crown thereon. Any excess of the post will be cut off. One length of the device will be longer to accommodate the longer roots in anterior teeth. Another length will be shorter to accommodate smaller roots in the molar region.

Figure 3:
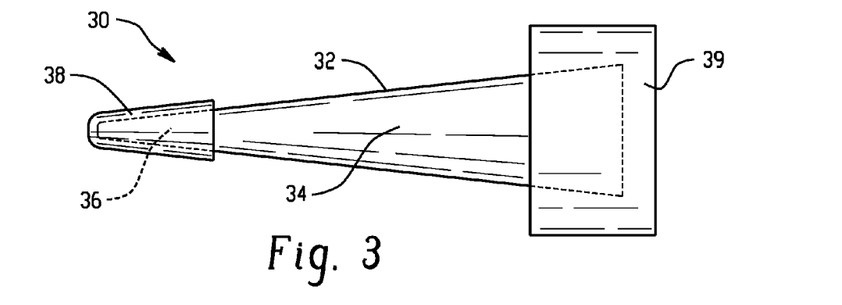
FIG. 3 is an elevational view of an alternate embodiment of an alternate carrier in accordance with the invention.

FIG. 3 shows a post unit 30 comprises a post section 32 fabricated of fiber reinforced composite material. Post section 32 includes main body 34 and carrier 36. Carrier 36 is coated with a filling material to obtain cone section 38 thereon. As shown in the drawing, main body 34 is tapered to provide ease of placement into the canal. The cross-section of post unit 30 may be smaller than the cross-section of a standard post to fit in thinner or smaller auxiliary canals which are normally filled with a thermoplastic material. Accordingly, post unit 30 can act as an obturator. As an obturator, better support is provided due to the fiber-reinforced composite structural component 34 upon which cone section 38 is applied in comparison to using only a thermoplastic material as an obturator. Moreover, the obturator may be easily cemented in place in the canal. Post unit 30 may also include a handle 39 which is beneficial when the post unit is used as an obturator. Handle 39 may be any filled or unfilled polymeric material, such as those mentioned above and used in the fabrication of the post.

Figure 4:
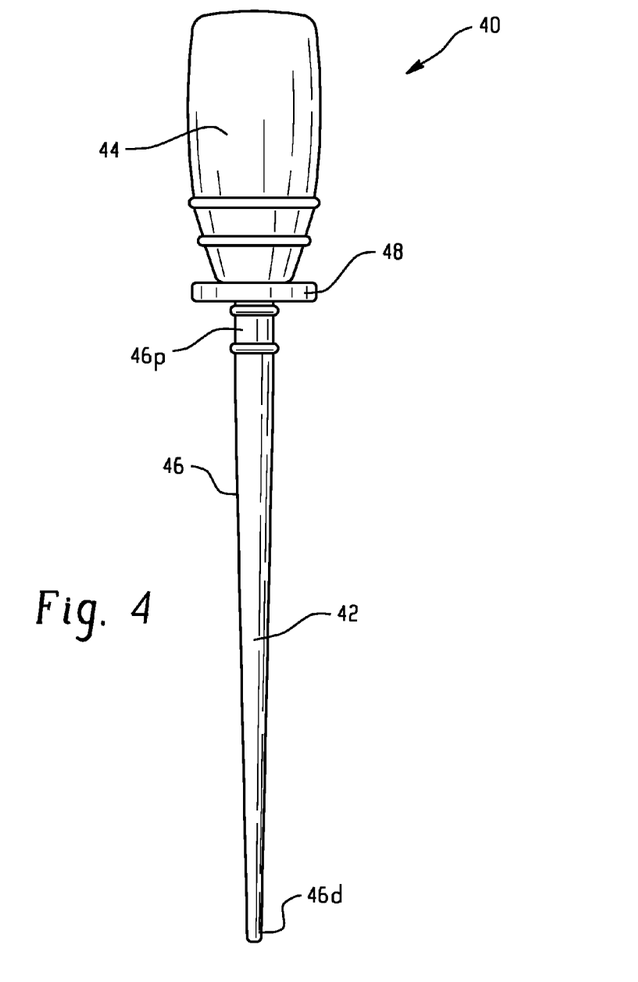
FIG. 4 is an elevational view of yet another alternative embodiment of the invention.

FIG. 4 is directed to an obturator 40 having filling core or point 42 and a handle 44. Filling core 42 is a shaft 46 having a proximal end 46*p* and a distal end 46*d* that fits in a root canal. A sliding support 48 is positioned between shaft 46 and handle 44 to serve as an indicator of the depth of the canal and to help maintain the obturator in place. After the appliance is inserted in the canal, sliding support 48 is moved to the point at the top of the canal. Obturator 40 is cut off at the point desired to fit the canal. Filling core 42 containing a biodegrable thermoplastic polymer and optionally, a bioactive filler, in the form of shaft 46, fills the canal. The filling core 42 and handle 44 are a single unit fabricated of a biodegradable thermoplastic polymer and optionally, a bioactive filler. Alternatively, the filling core is made of a biodegradable thermoplastic polymer and optionally, a bioactive filler and the handle may be fabricated of any know material including but not limited to metal, plastic, composite, ceramic, glass or polymeric material.

The compositions of the inventive materials have a radiopacity similar to gutta percha materials.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An obturator for filling a root canal comprising:
a handle; and
a shaft;
wherein the shaft is fabricated of a filling core in the form of the shaft, which filling core is designed to, by itself, fit and fill the root canal; and
wherein the filling core consists of a filling material comprising a biodegradable thermoplastic polymer selected from the group consisting of polylactides, polyglycolides, polycaprolactones, polyanhydrides, polyorthoesters, polydioxanones, polyketals, polyphosphazenes, polyhydroxybutyrates, polyhydroxyvalerates, polyalkylene oxalates, polyethylene oxides, polyalkylene succinates, poly(malic acid) polymers, polymaleic anhydrides, poly(methylvinyl) ethers, poly(amino acids), chitin, chitosan, or copolymers thereof, terpolymers thereof, combinations thereof, and mixtures thereof, and wherein the filling material further comprises a bioactive filler.

2. The obturator of claim 1 wherein the bioactive filler comprises bioglass, calcium phosphate, Portland cement, hydroxyapatite, tricalcium phosphate, a di- or polyphosphonic acid, an anti-estrogen, a sodium fluoride preparation, a substance having a phosphate to calcium ratio similar to natural bone, or mixtures thereof.

3. The obturator of claim 1 wherein the obturator further comprises a sliding support positioned between the shaft and handle capable of indicating the depth of a root canal and for maintaining the obturator in place in the root canal, wherein the sliding support is capable of slidably moving along the shaft to the point at the top of the root canal after the obturator is inserted in the root canal.

4. The obturator of claim 1 wherein the obturator is capable of being inserted in a root canal to fill the root canal, and a means for indicating the depth of the root canal, after the obturator is inserted in the root canal, is capable of being slidably moved to the point at the top of the root canal and, the obturator is designed to be capable of thereafter being cut off at a point desired to fit the canal.

5. An obturator for filling a root canal comprising:
a handle; and
a shaft;
wherein the shaft consists of a filling core that is designed to, by itself, fit and fill a root canal wherein the filling core consists of a filling material comprising a biodegradable thermoplastic polymer selected from the group consisting of a polylactide, polyglycolide, polycaprolactone, copolymer thereof, and combination thereof; and
wherein the filling material further comprises a bioactive filler selected from the group consisting of bioglass, calcium phosphate, Portland cement, hydroxyapatite, tricalcium phosphate, a di- or polyphosphonic acid, an anti-estrogen, a sodium fluoride preparation, a substance having a phosphate to calcium ratio similar to natural bone, and mixtures thereof.

6. The obturator of claim 5 wherein the obturator further comprises a sliding support positioned between the shaft and handle capable of indicating the depth of a root canal and for maintaining the obturator in place in the root canal; and wherein the obturator is capable of being inserted in the root canal to fill the root canal and the sliding support, after the obturator is inserted in the root canal, is capable of being slidably moved along the shaft to the point at the top of the root canal, and wherein the obturator is thereafter capable of being cut off at a point desired to fit the root canal.

7. An obturator for filling a root canal comprising:
a handle; and
a shaft consisting of a filling core;
wherein the filling core is designed to, by itself, fit and fill a root canal wherein the filling core consists of a filling material comprising a biodegradable thermoplastic polymer, and wherein the biodegradable thermoplastic polymer is selected from the group consisting of polylactides, polyglycolides, polycaprolactones, polyanhydrides, polyorthoesters, polydioxanones, polyketals, polyphosphazenes, polyhydroxybutyrates, polyhydroxyvalerates, polyalkylene oxalates, polyethylene oxides, polyalkylene succinates, poly(malic acid) polymers, polymaleic anhydrides, poly(methylvinyl) ethers, poly(amino acids), chitin, chitosan, or copolymers thereof, terpolymers thereof, combinations thereof, and mixtures thereof;
wherein the obturator further comprises a sliding support positioned between the shaft and handle capable of indicating the depth of a root canal and for maintaining the obturator in place in the root canal; and wherein the obturator is capable of being inserted in the root canal to fill the root canal and the sliding support is capable of being slidably moved along the shaft to the point at the top of the root canal after the appliance is inserted in the root canal, and wherein the obturator is thereafter capable of being cut off at a point desired to fit the root canal.

* * * * *